United States Patent
von der Heyde

[19]

[11] Patent Number: 6,100,501
[45] Date of Patent: *Aug. 8, 2000

[54] TICK REMOVAL DEVICE WITH HEATING AND ILLUMINATION

[76] Inventor: Christian P. von der Heyde, 182 Great Hill Rd. Ext., East Sandwich, Mass. 02537

[*] Notice: This patent is subject to a terminal disclaimer.

[21] Appl. No.: 09/262,268

[22] Filed: Mar. 4, 1999

Related U.S. Application Data

[63] Continuation-in-part of application No. 09/039,451, Mar. 16, 1998, Pat. No. 5,998,762.

[51] Int. Cl.⁷ .............................. A61B 17/50; H05B 1/00
[52] U.S. Cl. .................... 219/229; 219/230; 219/220; 219/231; 43/134; 606/131; 606/28; 362/120; 362/109
[58] Field of Search ................... 219/229, 227, 219/230, 231, 220, 228; 606/131, 210, 211, 51, 52, 205, 206, 28–31, 45; 294/99.2, 93, 94, 100, 119.1, 166, 168; 43/134, 135; 392/409; 362/119–120, 109

[56] References Cited

U.S. PATENT DOCUMENTS

| | | | |
|---|---|---|---|
| 2,620,692 | 12/1952 | Marshall, III | 219/227 |
| 4,176,273 | 11/1979 | Fujie et al. | 219/220 |
| 4,213,460 | 7/1980 | Weiner | 606/131 |
| 4,247,753 | 1/1981 | Jaronen | 219/230 |
| 4,539,987 | 9/1985 | Nath et al. | 392/421 |
| 4,883,942 | 11/1989 | Robak, Sr. et al. | 219/227 |
| 5,116,347 | 5/1992 | Butler | 606/131 |
| 5,276,306 | 1/1994 | Huffman | 219/229 |
| 5,447,511 | 9/1995 | Gadd | 606/131 |
| 5,554,161 | 9/1996 | Thibeault | 606/131 |
| 5,556,563 | 9/1996 | von der Heyde et al. | 219/227 |
| 5,607,434 | 3/1997 | Alvino | 606/131 |
| 5,843,094 | 12/1998 | Saylor | 606/131 |
| 5,998,762 | 12/1999 | von der Heyde | 219/229 |

FOREIGN PATENT DOCUMENTS

| | | | |
|---|---|---|---|
| 748591 | 12/1966 | Canada | 219/227 |
| 105756 | 7/1898 | Germany | 219/227 |
| 657147 | 9/1951 | United Kingdom | 219/230 |

*Primary Examiner*—John A. Jeffery
*Attorney, Agent, or Firm*—William Nitkin

[57] ABSTRACT

A device for removal of a tick from the skin of a host and alternately to be used as a flashlight, such device having an open-ended casing for receiving the tick in a V-shaped alignment guide and slot defined in the casing, such tick to be trapped in the slot with structure to apply heat from an illuminating heating element in proximity to the tick to cause it to release its grip from the skin of the host after which it can be removed, with such illuminating heating element also acting as the light source when the device is used in its alternate flashlight mode.

4 Claims, 3 Drawing Sheets

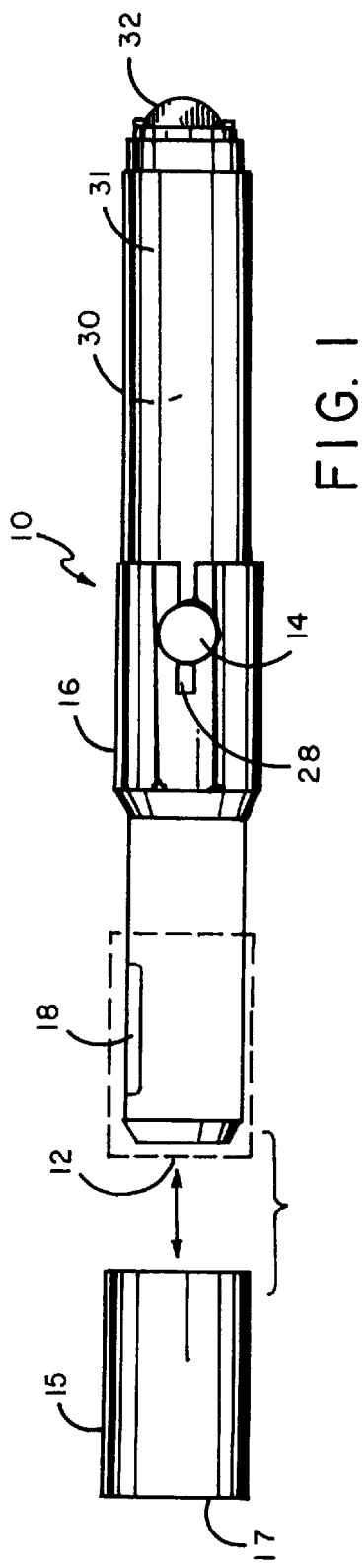
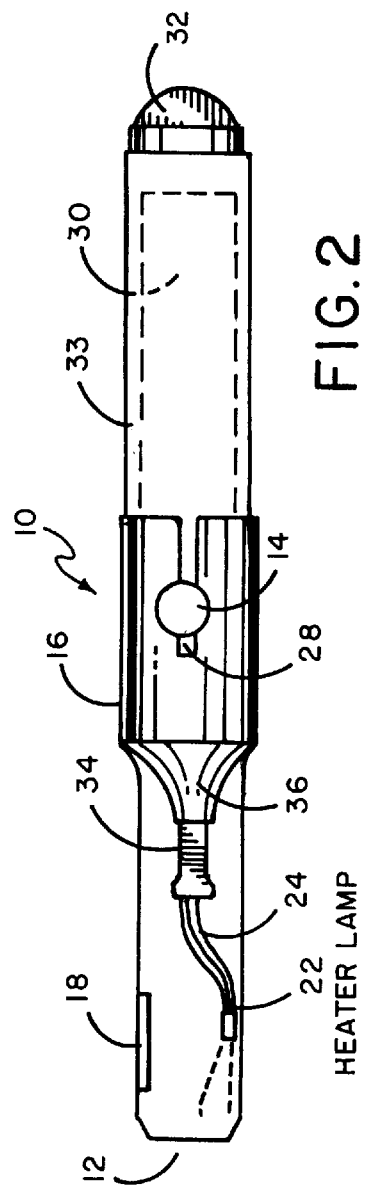
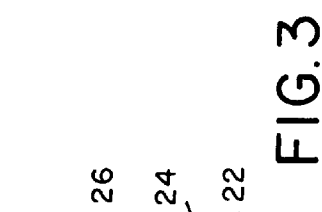

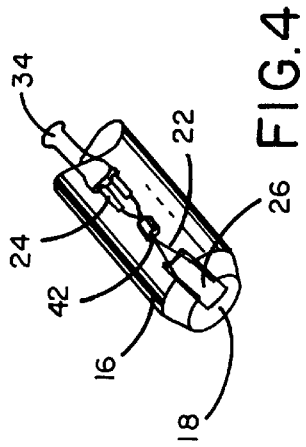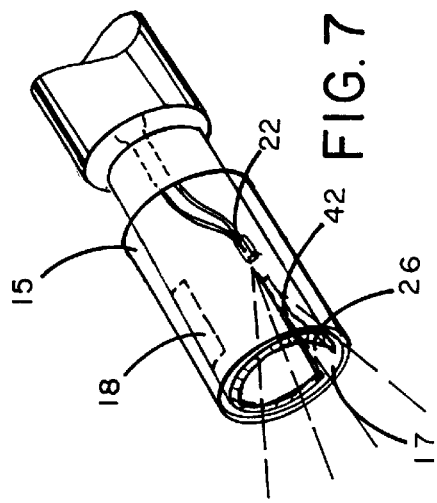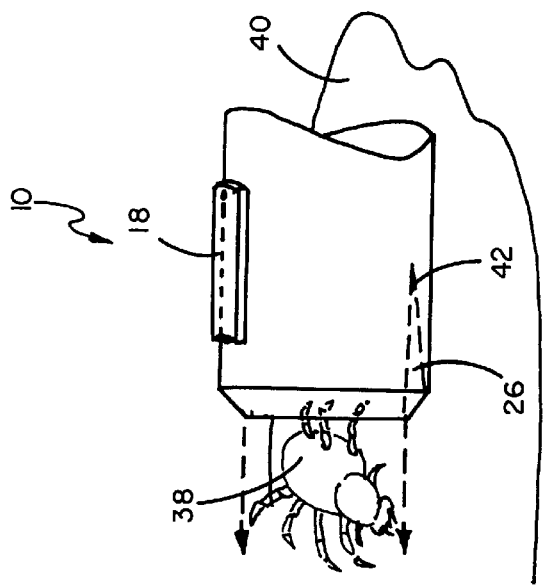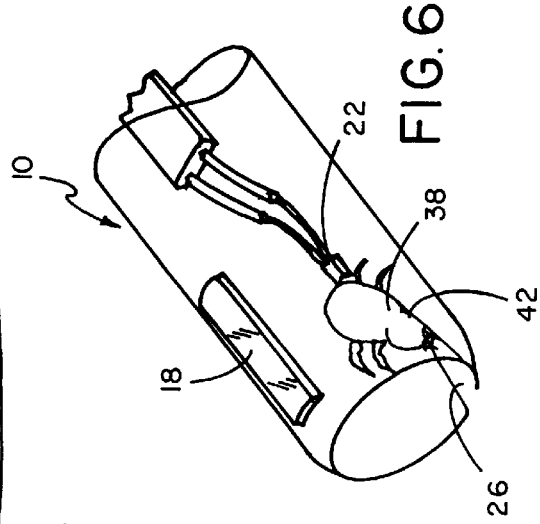

TICK REMOVAL DEVICE WITH HEATING AND ILLUMINATION

This application is a continuation-in-part of my prior application entitled Tick Removal Device and Method, Mar. 16, 1998, Ser. No. 09/039,451, now U.S. Pat. No. 5,998,762 issued Dec. 12, 1999.

BACKGROUND OF THE INVENTION

1. Field of the Invention

This invention resides in the area of devices for removing ticks from people and animals and more particularly relates to a device having a casing with a V-shaped alignment guide extending to a slot for engaging a tick within the slot and a heating element in close proximity to the tick for heating the tick to cause it to release its grip whereupon the tick can be removed, such heating element in one embodiment providing illumination when the device is alternately used as a flashlight.

2. Description of the Prior Art

Hand-held devices with tweezer-like arms for removing ticks are well known in the prior art. U.S. Pat. No. 5,556,563 by the present inventor discloses a device having first and second tweezer arms disposed within a casing with the tweezer arms extendible through the casing to grasp a tick. Other examples include U.S. Pat. No. 4,213,460 to Weiner describing forceps with an electrical current passing therethrough to provide heat, with the forceps having oppositely-aligned, cup-shaped members to surround and remove a tick. U.S. Pat. No. 4,979,771 to Childs, III also describes the use of cup members at the end of tweezer-like elements to surround a tick. U.S. Pat. No. 5,276,306 to Huffman teaches the use of a heated needle which, when poked into a tick, causes the tick to release its grip, and the tick can then be scooped off the skin by a spoon member disposed below the needle. A disadvantage of these tweezer-like gripping devices is their difficulty of use, as manipulating a device to grip a tiny tick requires a level of dexterity sometimes not possessed by the users of such devices.

Butler, U.S. Pat. No. 5,116,347 teaches a pair of pliers having two opposed jaws, convexly shaped in cross-section, which in use are closed around the head of a tick passing under its body with the jaws to close 0.006 inch apart so as not to snip off and leave the tick's head in the host's body. This device, though, due to its large jaw size and the closing movement, is difficult to align around a tick and keep the tick centered at the place where the jaws are to come together. A further problem with the Butler device seems to arise from the high degree of precision required in manufacturing the jaws of such a pliers-type tool. Examples of such devices tried by Applicant had their jaws come completely together in normal operation, leaving no space therebetween. Thus in practice the jaws of such devices would snip off a tick's head and not work as described in the Butler patent.

Another prior art patent is Thibeault, U.S. Pat. No. 5,554,161 which teaches away from pliers-type tools. It uses a V-shaped slit in the side of a spoon-shaped member and a second spoon-shaped member that rotates thereover but does not completely overlap and close the slit so as to capture a tick therebetween. The spoon members can be spring-loaded so as to close laterally around the tick quickly and easily. However, the need for lateral alignment of the moving parts of the device can complicate the process, making it difficult for some people to properly align and successfully use the Thibeault device.

SUMMARY OF THE INVENTION

It is an object of this invention to provide a portable, effective device to remove a tick attached to the skin of a person or animal, such device having a casing with a unique tapered V-shaped alignment guide and communicating slot for forwardly engaging and grasping a tick and an illuminating heating element in close proximity to the held tick for causing the tick to release its grip. In operation, the device is slid forward across the skin to grasp a tick, the tick becoming trapped in the narrow slot at the end of the V-shaped alignment guide defined in the front portion of the bottom of the casing. The user then activates the illuminating heating element which is either in contact with, or in close proximity to, the trapped tick. The heat causes the tick to release its grip on the person or animal, and the tick can then be conveniently lifted away in the casing for easy disposal.

It is a further object of this invention to provide a heat-producing tick removal device where the illuminating heating element during use of the device is safely kept away from the skin of the person or animal, the skin being shielded by the bottom part of the plastic casing.

It is a still further object of this invention for such device to be usable as a flashlight.

It is yet a further object of this invention to provide a portable, inexpensive, easily manipulatable device which can operate on a single AA battery.

BRIEF DESCRIPTION OF THE DRAWINGS

FIG. 1 illustrates a side view of the tick removal device of this invention with flashlight cover shown separated therefrom.

FIG. 2 illustrates a side view of the device with the casing shown as being transparent.

FIG. 3 illustrates a front cross-sectional view through the device of this invention.

FIG. 4 illustrates a bottom front end perspective sectional view of the device of this invention.

FIG. 5 illustrates a perspective sectional view of the front end of the casing as it is being slid toward a tick to engage the tick in the narrow slot at the end of the V-shaped alignment guide.

FIG. 6 illustrates the view of FIG. 5 showing the tick caught inside the slot at the end of the V-shaped alignment guide disposed in the casing of the device.

FIG. 7 illustrates the view of FIG. 6 with the flashlight cover in place at the front end of the device.

DESCRIPTION OF THE PREFERRED EMBODIMENT(S)

Figure 8:
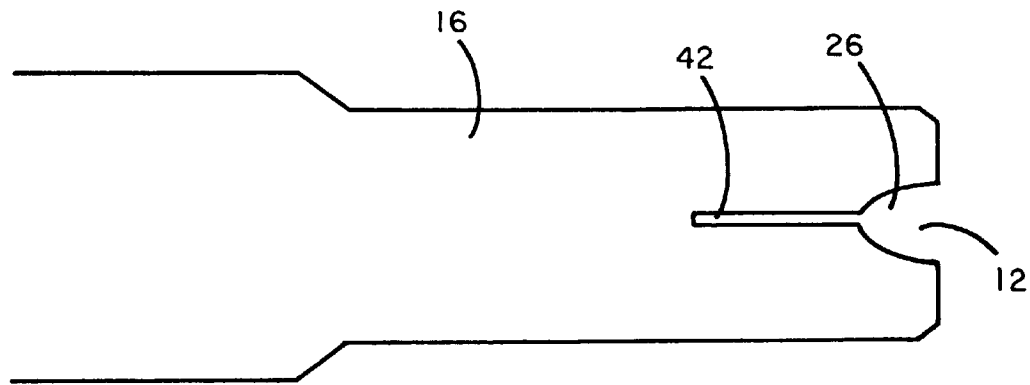
FIG. 8 illustrates an enlarged bottom sectional view of the front end of the casing, showing the V-shaped alignment guide and slot.

FIG. 1 illustrates a side view of the tick removal device 10 of this invention showing casing 16 which is slidably mounted on the body 30 of device 10. Casing 16 is hollow on the inside and can be made of any lightweight durable plastic or equivalent material. Casing 16 has an opening 12 at its front end where the tick is entered into the casing by manually moving the casing forward to align its open end with the tick, and then moving the casing forward toward the tick so that the tick passes first into the alignment guide, which can be V-shaped or U-shaped, and then into the slot, as described in more detail below. In a preferred embodiment, from opening 12 in a rearward direction, casing 16 has a constant diameter of approximately ½ inch for a length of approximately two inches, the diameter thereafter increasing to accommodate a close fit between casing 16 and body 30 of the device. As seen in FIGS. 1 and 2, casing 16 has an aperture 28 defined within its top portion which allows for movement of activating button 14 therein. Observation means such as window 18 defined in the top front portion of said casing can be provided. In one embodiment, magnification means such as a magnifying glass can be mounted in window 18 on the top of casing 16 near the front end to magnify the size of a tick, thereby facilitating observation and capture of the tick by the user of the device. Observation means can also be provided by constructing the casing out of transparent plastic. A hollow flashlight cover 15 is shown at the front of device 10 and can be slid onto casing 16 to cover V-shaped alignment guide 26 and slot 42, as seen in FIG. 7, and window 18. The front of flashlight cover 15 has flashlight aperture 17 defined therein to direct light out flashlight aperture 17 when the device is used as a flashlight. When the device is to be used as a tick remover, flashlight cover 15 is pulled forward off the front end of casing 16 to expose V-shaped alignment guide 26, slot 42 and window 18.

As seen in FIG. 2, body 30 of the device includes heating element 22, which can be of the illuminating type, which protrudes into the hollow casing. Illuminating heating element 22 includes heating element support 34 which can be made of plastic with wires running therethrough. Leads 24 emerge from heating element support 34, which leads are connected to illuminating heating element 22. Illuminating heating element 22 can be a high-intensity light bulb such as a small quartz halogen light or equivalent that when lit, produces heat and is part of a circuit which is completed by button 14 which activates as a switch to direct current from a power source, such as a AA battery, in body 30 to illuminating heating element 22 which is used to direct heat to a trapped tick. The circuit is formed between illuminating heating element 22, leads 24, and wires (not shown) which run through heating element support 34 and tapered section 36 of body 30 and are connected to a battery power source with a switch to open and close the circuit. As seen in FIG. 3, a foil strip 20 or equivalent insulative material covers the bottom of casing 16, thereby preventing charring or melting of the casing from the heat produced by illuminating heating element 22.

Body 30 in a preferred embodiment can be generally tubular in shape and contains battery chamber 31 which receives a AA battery 33 which serves as the power source for the circuit. Battery cover 32, as seen in FIGS. 1 and 2, fits over the rear end of the device. Heating and illumination occur when the user pushes on activating button 14 which closes a switch, completing the circuit between the battery and the illuminating heating element. As seen in FIG. 3, activating button 14 protrudes above casing 16 of the device. Although a button activation means is illustrated, other well-known activation means can be utilized in the device of this invention.

FIG. 4 shows alignment guide 26 which can be a V-shaped, U-shaped or equivalent shape to direct the tick into elongated slot 42 in plastic casing 16 which is used to trap the tick. The term "V-shaped" is used herein to define a tapered opening which is forwardly advanced by the user around the tick to easily direct the tick into slot 42. Disposed at the bottom portion of open front end 12 of casing 16 is V-shaped alignment guide 26 which progressively narrows from open front end 12 until it opens into slot 42. The alignment guide and narrow slot are essentially cut out of plastic casing 16 and are fixed in shape and are not adjustable. The alignment guide and slot are designed to guide, catch and hold the tick around its head under its body in slot 42 either in contact with, or in close proximity to, illuminating heating element 22. The thickness of the casing must be thin enough to pass between the junction of the tick's head with its body which junction forms a convenient place to catch and retain the tick until it is removed by the user of the device of this invention.

In operation of the device after removal of flashlight cover 15, casing 16 is slid forward, as seen in FIG. 5, along skin 40 of the host toward tick 38 with the user manually directing the device such that the tick passes into V-shaped alignment guide 26 and then into slot 42. The user can look through window 18 located directly over V-shaped alignment guide 26 to more easily aim the device as it is moved toward the tick. The narrowing shape of alignment guide 26 further facilitates directing the device toward the tick. As the casing is moved with the alignment guide advancing around the tick, eventually the distance between the sides of the V-shaped alignment guide adjacent to the tick becomes narrower and the tick passes into slot 42, the sides of which can snugly catch the tick at the junction of the tick's head with its body. Illuminating heating element 22 produces a surge of heat when the user presses button 14 to activate illuminating heating element 22 which is positioned to the rear of slot 42 to be close to, or in contact with, the tick's body once the tick is trapped in slot 42. The intense heat causes the tick to release its grip on the skin of the host whereupon the tick, still trapped in the slot, can be lifted off the skin and disposed of.

In a preferred embodiment the width of V-shaped alignment guide 26 at the front end opening of the casing is approximately ⅛–¼ inch, and the sides of the alignment guide are angularly tapered for a distance of approximately ⅛–¼ inch at which point the sides come together to form a substantially parallel-sided slot 42 which slot has an open front end and a closed rear end and which is approximately a minimum of ⅛ inch long with ½ inch working well and 0.006–0.012 inch wide.

FIG. 8 illustrates an enlarged bottom view of the front end of the casing, better showing alignment guide 26 extending into substantially parallel-sided slot 42. As seen in FIG. 6, the head area of tick 38 is shown trapped in slot 42.

Figure 9:
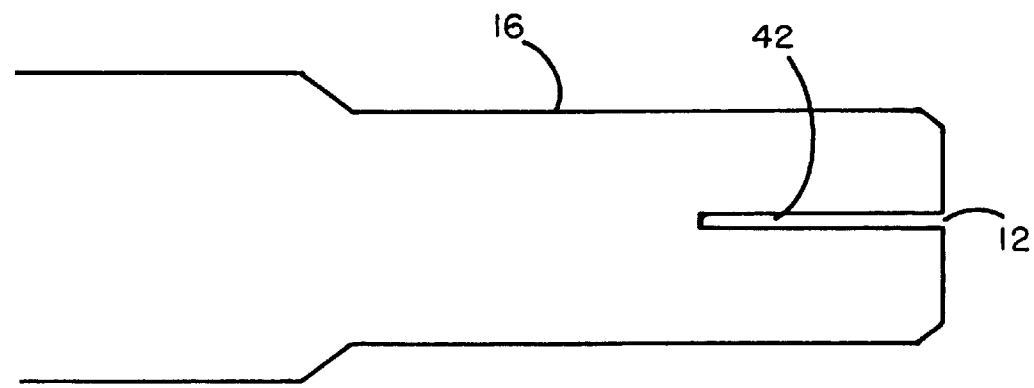
FIG. 9 illustrates an enlarged bottom sectional view of the front end of the casing of an alternate embodiment of the device, showing the slot without an alignment guide.

In some embodiments of the device, as shown in FIG. 9, only slot 42 is provided to trap the tick without an alignment guide if the user of the device is able to carefully align the tick in the slot.

When the device is used in its flashlight mode with flashlight cover 15 in place at the front end of the device, the user presses button 14 and illuminating heating element 22 is activated, shining light through open flashlight aperture 17 of flashlight cover 15.

Although the present invention has been described with reference to particular embodiments, it will be apparent to those skilled in the art that variations and modifications can be substituted therefor without departing from the principles and spirit of the invention.

I claim:

1. A device for removing a tick from the skin of a host for use by a user, comprising:

a casing having a front end and a rear end, said casing having an aperture defined therein at its front end;

a V-shaped alignment guide and elongated parallel-sided slot defined in said casing at said front end thereof, said V-shaped alignment guide having a first end disposed at said front end of said casing and a second end, said slot having an open first end and a closed second end, said first end of said V-shaped alignment guide having a width, said width of said first end of said V-shaped alignment guide being widest at said front end of said casing and narrowing at said second end of said V-shaped alignment guide said second end of said V-shaped alignment guide in communication with said open first end of said slot, said V-shaped alignment guide for receiving a tick therein to direct a tick into said slot where a tick is trapped;

illuminating heating means disposed in proximity to said second end of said slot, said illuminating heating means when activated to cause discomfort to a tick to cause a tick to release its grip on the skin of said host, said illuminating heating means having user-operated activation means associated therewith; and window means disposed in said casing above said V-shaped alignment guide and slot to aid said user in observing the engagement of a tick within said slot.

2. The device of claim 1 further including magnification means disposed in said window means.

3. A device for removing a tick from the skin of a host for use by a user, comprising:

a casing having a front end and a rear end, said casing having an aperture defined therein at its front end;

a V-shaped alignment guide and elongated slot defined in said casing at said front end thereof said V-shaped alignment guide having a first end disposed at said front end of said casing and a second end, said slot having an open first end and a closed second end, said first end of said V-shaped alignment guide having a width, said width of said first end of said V-shaped alignment guide being widest at said front end of said casing and narrowing at said second end of said V-shaped alignment guide said second end of said V-shaped alignment guide in communication with said open first end of said slot;

illuminating heating means disposed in proximity to said second end of said slot, said illuminating heating means having user-operated activation means associate therewith;

window means disposed in said casing said V-shaped alignment guide and slot to aid said user in observing the engagement of a tick within said slot;

magnification means disposed in said window means; and a removable hollow flashlight cover having a front end, said flashlight cover positionable over said casing at said front end of said device, said flashlight cover when in position on said casing covering said window means, said V-shaped alignment guide and said slot, said flashlight cover having an aperture defined in its front end to direct light from said illuminating heating means therethrough so that said device can be used as a flashlight.

4. The device of claim 3 wherein said V-shaped alignment guide is approximately $1/8$–$1/4$ inch wide at said front end of said casing and extends rearwardly approximately $1/8$–$1/4$ inch to said first end of said elongated slot, said elongated slot having substantially parallel sides extending rearwardly approximately a minimum of $1/8$ inch in length and approximately 0.006–0.012 inch in width.

* * * * *